United States Patent [19]
Schmid et al.

[11] Patent Number: 5,733,658
[45] Date of Patent: Mar. 31, 1998

[54] LUSTER PIGMENTS BASED ON REDUCED TITANIA-COATED SILICATE-BASED PLATELETS

[75] Inventors: Raimund Schmid, Neustadt; Claus Kaliba, Neuhofen; Norbert Mronga, Dossenheim; Werner Ostertag, Grünstadt; Helmut Schmidt, Osthofen; Juan Antonio Gonzalez Gomez, Ludwigshafen; Hermann Bidlingmaier, Offenburg; Raymond Ellinghoven, Marbach, all of Germany

[73] Assignee: BASF Aktiengesellschaft, Ludwigshafen, Germany

[21] Appl. No.: 623,785

[22] Filed: Mar. 29, 1996

[30] Foreign Application Priority Data

Mar. 30, 1995 [DE] Germany .................. 195 11 696.8

[51] Int. Cl.$^6$ .................. B32B 5/16; B05D 3/04
[52] U.S. Cl. .................. 428/404; 427/331; 427/335; 427/337; 428/701; 428/702
[58] Field of Search .................. 428/403, 404, 428/702, 407, 701; 427/331, 335, 337, 398.1

[56] References Cited

U.S. PATENT DOCUMENTS

| | | | |
|---|---|---|---|
| 3,087,827 | 4/1963 | Klenke, Jr. et al. | 106/291 |
| 4,076,555 | 2/1978 | Chu et al. | 148/1.5 |
| 4,192,691 | 3/1980 | Armanini | 106/291 |
| 4,565,581 | 1/1986 | Bernhard | 106/308 B |
| 4,623,396 | 11/1986 | Kimura et al. | 106/291 |
| 4,948,631 | 8/1990 | Ostertag et al. | 427/208 |
| 5,061,317 | 10/1991 | Korpi et al. | 106/417 |
| 5,116,664 | 5/1992 | Kimura et al. | 428/216 |
| 5,156,889 | 10/1992 | DeLuca | 427/215 |
| 5,246,780 | 9/1993 | Farer et al. | 428/404 |
| 5,565,025 | 10/1996 | Schraml-Marth | 106/417 |

FOREIGN PATENT DOCUMENTS

| | | |
|---|---|---|
| 0 332 071 | 9/1989 | European Pat. Off. . |
| 0 525 526 | 2/1993 | European Pat. Off. . |
| 34 33 657 | 3/1985 | Germany . |
| 25 57 796 | 5/1985 | Germany . |
| 41 41 049 | 1/1994 | Germany . |
| 59-126468 | 7/1984 | Japan . |
| 60-184570 | 9/1985 | Japan . |
| 61-392 | 1/1986 | Japan . |
| WO 94/13489 | 6/1994 | WIPO . |

OTHER PUBLICATIONS

Japanese Patent Abstract, 61–192749, Feb. 21, 1985, English Abstract.
Patent Abstracts of Japan, vol. 9, No. 78 (C–274), Apr. 6, 1995.
Patent Abstracts of Japan, vol. 10, No. 31, (C–327), Feb. 6, 1986.
Database WPI, Week 8641 Derwent Pub., Ltd., London, GB; AN 86-267354—Aug. 1986.

*Primary Examiner*—H. Thi Le
*Attorney, Agent, or Firm*—Oblon, Spivak, McClelland, Maier & Neustadt, P.C.

[57] ABSTRACT

Luster pigments obtainable by treating titania-coated silicate-based platelets at from 400° to 900° C. with a gas mixture comprising a vaporized organic compound and ammonia are useful for coloring paints, inks, including printing inks, plastics, glasses, ceramic products and decorative cosmetic preparations.

5 Claims, No Drawings

LUSTER PIGMENTS BASED ON REDUCED TITANIA-COATED SILICATE-BASED PLATELETS

The present invention relates to novel luster pigments obtainable by treating titania-coated silicate-based platelets at from 400° to 900° C. with a gas mixture comprising a vaporized organic compound and ammonia.

BACKGROUND OF THE INVENTION

1. Field of the Invention

The present invention further relates to a process for producing these luster pigments and to their use for coloring paints, inks, including printing inks, plastics, glasses, ceramic products and decorative cosmetic preparations.

2. Description of the Related Art

Reduced titania-coated mica pigments whose $TiO_2$ coating comprises or has been wholly converted to reduced titanium species (oxidation state of the titanium: from <4 to 2) have long been known as "dark pearl luster pigments" for the blue to black hue range, and are notable for good hiding power, color strength and luster.

It is known to prepare said "dark" pearl luster pigments by treating titania-coated mica pigments with reducing gases at temperatures from 600° to 900° C.

The reducing gases which have been used are predominantly ammonia and ammonia/nitrogen mixtures. The products obtained are described as blue, bluish black or black and the reduced species as lower titanium oxides such as $Ti_3O_5$, $Ti_2O_3$ to TiO, titanium oxynitrides and also titanium nitride (JP-A-164 653/1983, JP-A-126 468/1984, JP-A-184 570/1985, DE-A-34 33 657 and EP-A-332 071).

JP-A-192 749/1985 also uses hydrogen and propane as reducing gases, the reduction with propane producing black pigments which are slightly electroconductive owing to the presence of carbon.

Furthermore, EP-A-525 526 describes the reaction of titania-coated mica pigments with propane at 850° C., which is said to bring about not only a deposition of carbon but also a reduction of the titanium.

Similarly, U.S. Pat. No. 3,087,827 discloses the coating of titania-coated mica pigments with carbon by pyrolysis of gaseous hydrocarbons in the presence of the mica pigments or, if hydrocarbons which are liquid at room temperature are used, formation of a pigment/hydrocarbon paste and subsequent pyrolysis at from 700° to 950° C.

Finally, carbonaceous mica pigments are also described in DE-A-25 57 796 and 41 41 049.

In said DE-A-25 57 796, titania-coated mica is coated with a further, soot-containing titanium dioxide layer by dispersing mica pigment and soot (carbon black) in aqueous phase, applying a soot-containing titanium hydroxide layer by hydrolysis of titanium tetrachloride, and then drying the pigment.

DE-A-41 41 049 discloses coating titania-coated mica with carbon by application of an aqueous sugar film and subsequent thermolysis at from 400° to 500° C.

These mica pigments with carbon or carbonaceous layers likewise exhibit good hiding power, color strength and luster.

However, the prior art pigments are unsatisfactory in several respects in that they have coloristic and/or application defects, depending on the manner of manufacture.

For instance, the reduction of titania-coated mica interference pigments with ammonia, hydrogen or hydrocarbons produces products with an intensive color only when the interference color of the mica substrate coincides with the absorption color of the reduction products.

Since the reduced titanium species such as $Ti_2O_3$ have a blue color, luster pigments with an intensive blue color are obtained only using $TiO_2$-mica pigments with a blue interference color.

Reducing, by contrast, a red-reflecting interference pigment, for example, the mixing of interference color and absorption color will result in an unattractive pigment having a brown masstone color. In general, the reduction of $TiO_2$-mica pigments which do not have a blue reflection color always produces unclean hues.

In addition, titania-coated mica pigments reduced with ammonia or hydrogen, in particular, generally have poor condensation water resistance in paints; that is, water vapor will produce irreversible decolorations (whitenings).

It is true that carbon-coated $TiO_2$-mica pigments as described for example in U.S. Pat. No. 3,087,827 do not have the above-described coloristic defects, since intensively colored pigments can usually be obtained over the entire hue range, but these pigments fall a long way short of today's fastness requirements.

Luster pigments incorporating carbon black pigments in the $TiO_2$ layer frequently exhibit poor abrasion resistance in respect of the carbon black particles, which manifests itself in the carbon black bleeding out in the course of the luster pigments being dispersed in paints. In addition, these pigments frequently show loss of luster on incorporation into paints due to the presence of free, unincorporated carbon black particles which can only be removed by costly sedimentation techniques.

SUMMARY OF THE INVENTION

It is an object of the present invention to provide pigments which are free of the defects mentioned.

We have found that this object is achieved by the above-defined luster pigments.

We have also found a process for producing these luster pigments, which comprises treating titania-coated silicate-based platelets at from 400° to 900° C. with a gas mixture comprising a vaporized organic compound and ammonia.

The invention further provides the use of the above-defined bluish luster pigments for coloring paints, inks, including printing inks, plastics, glasses, ceramic products and decorative cosmetic preparations.

DESCRIPTION OF THE PREFERRED EMBODIMENTS

Suitable platelet-shaped silicate-based substrate materials for the bluish luster pigments of the present invention include in particular light-colored or white micas, particularly preferably flakes of preferably wet-ground muscovite. It is of course also possible to use other natural micas, such as phlogopite or biotite, artificial micas, talc and glass flakes.

The substrate particles are coated with a layer which consists essentially of titanium dioxide and may contain minor proportions (generally <5% by weight) of further, preferably colorless, metal oxides such as zirconium dioxide, tin dioxide, aluminum oxide and silicon dioxide.

These pigments are generally known (cf. for example DE-A-14 67 468, DE-A-32 37 264 or DE-A-20 09 566). Titania-coated mica platelets are also commercially available under the names Iriodin® (E. Merck, Darmstadt), Flonac® (Kemira Oy, Pori, Finland) or Mearlin® (Mearl Corporation, Ossining, N.Y.).

The size of the substrate particles is not critical per se and can be adapted to the particular application. Typically, the platelet-shaped particles have average largest diameters of from about 1 to 200 µm, in particular from about 5 to 100 µm, and thicknesses of from about 0.1 to 1 µm, in particular about 0.5 µm. Their specific free surface area (BET) is customarily within the range from 1 to 15 $m^2/g$, in particular from 3 to 12 $m^2/g$.

The thickness of the $TiO_2$ layer determines the hue and, depending on the interference color desired, is generally from 40 to 300 nm, preferably from 50 to 200 nm (geometric layer thickness).

The luster pigments of the present invention can be obtained with advantage by the production process of the present invention by treatment at from 400° to 900° C. with a gas mixture comprising a vaporized organic compound and ammonia.

Suitable organic compounds include not only gaseous compounds but also compounds which are liquid or even solid at room temperature and can be vaporized.

Preference is given to hydrocarbons, especially saturated aliphatic $C_1$–$C_8$-hydrocarbons such as pentane, isopentane, neopentane, hexane, heptane and octane and also branched isomers thereof and very particularly methane, ethane, propane and butane and isomers thereof, also unsaturated aliphatic $C_2$–$C_4$-hydrocarbons such as ethene, propene, butene and isomers thereof and aromatic hydrocarbons such as benzene and toluene.

It is of course also possible to use mixtures of these hydrocarbons, as present in natural gas, for example.

It is also possible to use organic compounds which contain not only carbon and hydrogen but also oxygen and/or nitrogen, in which case, however, not more than one oxygen and/or nitrogen atom should be present in the molecule per carbon atom.

Examples of suitable compounds of this kind include $C_1$–$C_5$-alcohols such as methanol, ethanol, propanol and isopropanol, $C_3$–$C_7$-ketones such as acetone, di-$C_1$–$C_2$-alkyl ethers such as dimethyl and diethyl ether and cyclic ethers such as tetrahydrofuran and also mono-$C_1$–$C_5$-alkylamines and monoarylamines such as methylamine, ethylamine, propylamine and aniline, which can also be used alone, without ammonia, if the carbon/nitrogen ratio conforms to the desired composition of the reducing gas mixture. Generally, however, amines are more difficult to handle.

The volume ratio of the preferred components in the reducing gas mixture, ammonia and hydrocarbon, can be widely varied (in principle within the range from 80:20 to 1:99) and must be adapted in each case to the desired product properties, which are also influenced by the reaction time and the reaction temperature.

Carbon-richer and hence darker luster pigments are preferably produced at higher hydrocarbon contents (generally >50% by volume, based on the total volume of reducing gas), but also on using higher alkanes (e.g. propane instead of methane), at longer reaction times (from about 5 to 10 h) and moderate reaction temperatures (from about 400° to 800° C.).

Carbon-leaner, lighter luster pigments are conversely obtained in particular at lower hydrocarbon contents (generally <50% by volume, based on the total volume of reducing gas) and also on using lower alkanes (in particular methane or ethane), shorter reaction times (from about 1 to 2 h) and higher reaction temperatures (from about 750° to 900° C.).

Typically the carbon content of the luster pigments of the present invention is from 0.1 to 50% by weight. To produce colored luster pigments, a carbon content of from 0.2 to 10% by weight, preferably of from 0.2 to 5% by weight, is particularly suitable. Carbon contents >10% by weight generally produce dark luster pigments having a weak color shimmer and particularly high carbon contents (>25% by weight) produce black luster pigments.

In the case of the particularly suitable hydrocarbons methane, ethane and propane, the volume ratio of ammonia:hydrocarbon is preferably within the range from 4:1 to 1:4, particularly preferably within the range from 3:2 to 2:3.

Advantageously the reducing gas mixture is diluted with an inert gas such as nitrogen. This is advisable in particular when the organic compound first has to be evaporated and is ideally carried into the reaction space by the inert gas stream. A particular advantage is a nitrogen content of from 10 to 60% by volume, based on the total amount of gas. However, it is also possible to use a gas mixture consisting of hydrocarbon and ammonia only.

The process of the present invention is generally carried out at from 400° to 900° C., preferably at from 600° to 800° C., particularly preferably at from 650° to 750° C.

Temperatures ≦800° C. in particular afford particularly condensation-water resistant (rating ≧4, gray scale of German Standard Specification DIN 54001; Cleveland Humidity Test) and weather fast (rating ≧4, gray scale of German Standard Specification DIN 54001; short weathering test), and hence also lightfast, luster pigments which are also very intensive in color and very clean in hue for the entire color gamut.

The action of the gas mixtures comprising organic compound (especially hydrocarbon) and ammonia also reduces (at least) in part the $TiO_2$ layer of the luster pigments of the present invention to form the reduced species described at the beginning. The degree of reduction increases with increasing reaction temperature and increasing reaction time; also on the increase, in parallel, is the nitrogen content of the luster pigments, i.e. the proportion of nitridic titanium compounds.

The process of the present invention can be carried out not only continuously, for example in a heated, inertized rotary tube oven fed with the mica pigment and with a mixture of the reducing gases with an inert gas, but also batchwise, for example in a heated, inertized rotary drum with gas inlet and outlet or a heated, inertized fluidized bed reactor, in which case it is advantageous for the mica platelets to come into contact with the reducing gas on all sides, which, in the rotary tube oven or in the rotary drum, is preferably achieved by means of trip strips.

After the reduction has ended, generally after 1–10 h, particularly 2–7 h, the luster pigment is preferably cooled down under an inert gas. If desired, a deagglomerating step can follow, for example in a mixer equipped with beater blades.

The luster pigments of the present invention are advantageously useful for many purposes, such as the coloring of plastics, glasses, ceramic products, decorative cosmetic preparations and in particular paints and inks, including printing inks, especially security inks (cf. WO-A-94/13489, where luster pigments are specifically used together with color pigments to produce forgeryproof documents). All industrially customary printing processes can be used, for example screen printing, intaglio printing, bronze printing, flexographic printing and offset printing.

For these purposes, the luster pigments of the present invention can also be used with advantage in a blend with transparent and hiding white, colored and black pigments and also conventional luster pigments.

Examples of suitable luster pigments include singly or multiply metal oxide-coated mica and metal pigments, uncoated metal pigments based on aluminum, black luster pigments, such as platelet-shaped graphite and magnetite pigments, and platelet-shaped metal oxide pigments, for example based on iron(III) oxide and bismuth oxychloride.

Suitable inorganic pigments include for example titanium oxides, doped titanium oxides such as nickel titanium yellow, iron oxides, bismuth vanadates, colored spinels, chromate and cadmium pigments.

Suitable organic pigments include for example monoazo pigments (e.g. products derived from acetoacetarylide derivatives or from β-naphthol derivatives), laked monoazo dyes such as laked β-hydroxynaphthoic acid dyes, disazo pigments, condensed disazo pigments, isoindoline derivatives, derivatives of naphthalene-dicarboxylic acid, derivatives of perylenetetracarboxylic acid, anthraquinone pigments, thioindigo derivatives, azomethine derivatives, quinacridones, dioxazines, pyrazoloquinazolones, indanthrone and phthalocyanine pigments.

EXAMPLES

Preparation and evaluation of luster pigments according to the present invention The luster pigments are prepared in a mechanically rotatable single-neck quartz round-bottom flask equipped with a gas inlet and outlet in the axis of rotation and enclosed by a clamshell oven.

Use in Paint

To evaluate the colorimetrics of the pigments in paint, 4 g each of the pigment samples were stirred into 96 g of a mixed polyester varnish having a solids content of 21% by weight and the mixture was dispersed using a propeller stirrer at 1500 rpm for 15 min. Thereafter this base coating was adjusted to a spray viscosity of 18 sec in DIN cup 4 (DIN 53 211) and sprayed onto an unprimed aluminum panel. Following a short flashoff time, a one-component clear varnish based on acrylate/melamine resin (47% by weight solids, adjusted to 23 sec DIN 4) was applied wet on wet. After 30 minutes flashoff at room temperature, the panel was baked at 130° C. for 30 min.

The CIELAB coordinates were subsequently measured with a Multiflash M45 goniospectrophotometer from Optronik (Berlin) at an angle difference of 20°, 45° or 75° to the specular angle. The color coordinates (L, a*, b*, HGD, C*) indicated in the table are based on the standard illuminant D65. L is the lightness, a* is the red or green content and b* is the blue or yellow content. HGD is the hue angle [*] and C* is the chroma.

Condensation Water Resistance Test

The condensation water resistance characteristics of the pigments in the paint were assessed using the Cleveland Humidity Test. The base-coated panels (in each case not only an unprimed aluminum panel but also an automotive body panel with the following coating build: bondered substrate (zinc phosphated steel)/cathodic electrocoating/polyester-acetobutyrate primer) were placed in a Cleveland Condensing Humidity Cabinet (Condensation Tester Q.C.T from The Q-Panel Company; Cleveland, Ohio, USA). The fully deionized water bath was adjusted to a temperature of 70° C. and the panels were continuously bedewed for 24 h at 100% relative humidity.

On completion of the condensation water exposure, the panels were dried off and without delay assessed in respect of a color change against the gray scale of German Standard Specification DIN 54001 (corresponding to ISO 105). On this scale, coatings without a change in color are rated 5 and coatings which have completely turned white are rated 1.

Weather Fastness Test

To assess the weather fastness, the coated panels (unprimed aluminum) were exposed for up to 80 d in a Xenotest 1200 from Heraeus (Hanau, Germany) in accordance with German Standard Specification DIN 53387-1-B-X ("Artificial weathering or ageing by exposure to filtered xenon arc radiation", April 1989).

3 NXe 4500 xenon lights are used, each with an irradiation output of 65–75 W/m$^2$ (Heraeus). The lights are rotated every 500 hours, each light being in effect replaced after 1500 hours of operation.

The exposure conditions used are as follows: rotary operation by spraying with DM water; rain cycle: 18 min wet/102 min dry; relative humidity in the wet phase: about 95%; and in the dry phase: 60–70%; black panel temperature: 63°–67° C.

The weathered panels were then assessed as above against the gray scale of German Standard Specification DIN 54001 (ISO 105).

EXAMPLE 1

75 g of a titania-coated mica pigment with a red reflection color (Iriodin® 221 Rutile Fine Red; E. Merck, Darmstadt, Germany) were inertized in the above-described apparatus by passing 15 l/h of nitrogen over the pigment for 1 hour. After heating to 700° C. a mixture of 5 l/h of ammonia, 5 l/h of propane and 5 l/h of nitrogen was passed through the apparatus for 2 h. The subsequent cooling down to room temperature took place under 15 l/h of nitrogen.

The pigment obtained had an intensive red color, a carbon content of 2.1% by weight, a nitrogen content <0.2% by weight, very good condensation water resistance (rating 4–5) and very good weather-fastness (80 d of weathering, rating 5).

COMPARATIVE EXAMPLE C1

Example 1 was repeated without propane.

The pigment hardly changed color, retaining its white masstone color (nitrogen content<0.2% by weight).

Because of the poor coloristics, the condensation water resistance and the lightfastness were not tested.

COMPARATIVE EXAMPLE C2

Example 1 was repeated without ammonia.

The pigment obtained had an intensive red color (carbon content 1.1% by weight), but was neither resistant to condensation water (rating 2) nor fast to weathering (20 d weathering, rating 1–2).

COMPARATIVE EXAMPLE C3

75 g of the mica pigment of Example 1 were reduced at 850° C. with 75 l/h of ammonia for 2 h.

The pigment changed from white to dirty brown. The red interference color disappeared (nitrogen content 1.7% by weight).

Because of poor coloristics, the resistance to condensation water and the weathering fastness were not tested.

TABLE

| Example | Colorimetric data | | | | |
|---|---|---|---|---|---|
| | HGD | C* | L | a* | b* |
| Measuring angle 20° | | | | | |
| 1 | 335.9 | 32.2 | 48.3 | 29.3 | −13.1 |
| C1 | 12.3 | 23.2 | 83.4 | 22.6 | 5.0 |
| C2 | 342.8 | 36.2 | 55.0 | 34.6 | −10.7 |
| C3 | 55.8 | 23.3 | 59.8 | 13.1 | 19.2 |
| Measuring angle 45° | | | | | |
| 1 | 336.1 | 14.0 | 18.6 | 12.8 | −5.7 |
| C1 | 107.1 | 12.2 | 63.9 | −3.6 | 11.7 |
| C2 | 345.1 | 15.6 | 24.6 | 15.1 | −4.0 |
| C3 | 30.1 | 7.1 | 23.3 | 6.1 | 3.5 |
| Measuring angle 75° | | | | | |
| 1 | 348.1 | 4.9 | 12.0 | 4.8 | −1.0 |
| C1 | 128.4 | 15.5 | 59.9 | −9.7 | 12.2 |
| C2 | 1.8 | 5.7 | 17.1 | 5.7 | 0.2 |
| C3 | 303.9 | 3.8 | 14.5 | 2.1 | −3.1 |

We claim:

1. Luster pigments obtained by treating titania-coated silicate-based platelets at from 400° to 900° C. with a gas mixture comprising a vaporized organic compound and ammonia.

2. Luster pigments as claimed in claim 1, wherefor the organic compound used is methane, ethane, propane, n-butane and/or isobutane.

3. Luster pigments as claimed in claim 1, wherein the silicate-based platelets are mica platelets.

4. A process for producing luster pigments as claimed in claim 1, which comprises treating titania-coated silicate-based platelets at from 600° to 900° C. with a gas mixture comprising a vaporized organic compound and ammonia.

5. A method of use of luster pigments as claimed in claim 1 for coloring paints, inks, including printing inks, plastics, glasses, ceramic products and decorative cosmetic preparations.

* * * * *